United States Patent [19]

Tschopp

[11] 4,268,591
[45] May 19, 1981

[54] MATERIAL FOR COLOR PHOTOGRAPHY

[75] Inventor: Paul Tschopp, Düdingen, Switzerland

[73] Assignee: Ciba-Geigy AG, Basel, Switzerland

[21] Appl. No.: 70,474

[22] Filed: Aug. 28, 1979

[30] Foreign Application Priority Data

Sep. 7, 1978 [CH] Switzerland .................. 9410/78

[51] Int. Cl.³ .............................................. G03C 7/00
[52] U.S. Cl. ..................... 430/17; 430/381;
430/388; 430/389; 430/548; 430/556; 430/557;
430/558
[58] Field of Search ............... 430/381, 388, 389, 475,
430/548, 556, 557, 558

[56] References Cited

U.S. PATENT DOCUMENTS

| | | | |
|---|---|---|---|
| 2,133,937 | 10/1938 | Middleton et al. | 430/475 |
| 2,140,540 | 12/1938 | Middleton et al. | 430/381 |
| 2,299,641 | 10/1942 | Middleton et al. | 430/381 |
| 3,050,394 | 8/1962 | Ben-Ezra et al. | 430/558 |
| 3,183,095 | 5/1965 | Klinger | 430/558 |
| 3,990,896 | 11/1976 | Arai et al. | 430/557 |
| 4,012,259 | 3/1977 | Okumura et al. | 430/557 |
| 4,095,983 | 6/1978 | Wolff et al. | 430/558 |
| 4,133,958 | 1/1979 | Boie et al. | 430/557 |
| 4,149,886 | 4/1979 | Tanaka et al. | 430/557 |

*Primary Examiner*—J. Travis Brown
*Attorney, Agent, or Firm*—Sprung, Felfe, Horn, Lynch & Kramer

[57] ABSTRACT

Light-sensitive recording material for color photography, which contains, in at least one silver halide emulsion layer, at least one yellow coupler of the formula

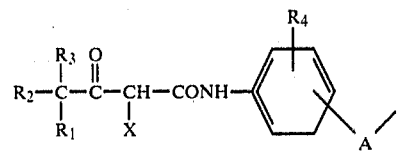

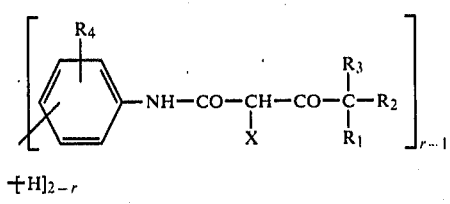

in which $R_1$ is alkyl, $R_2$ is alkyl or aryl and $R_3$ is substituted or unsubstituted alkyl, alkoxy or alkylmercapto, cycloalkylmercapto, aryl, aryloxy or arylmercapto, the sum of the carbon atoms in the substituents $R_1$, $R_2$ and $R_3$ being 3 to 30 and at least two of these substituents being able to form a cyclic radical together with the carbon atom to which they are bonded, the $R_4$s are each halogen, alkyl, alkoxy, halogenoalkyl, alkylsulfonyl or aryloxy, X is a radical detachable during the coupling reaction, A is a 5-membered, heterocyclic, unsaturated ring system which contains 2 or 3 hetero-atoms, at least one of which is a nitrogen atom, and can be fused with a benezene ring and which is substituted by at least one ballast group and r is 1 or 2.

The yellow couplers show high reactivity (high maximum density), which makes possible accelerated processing of the photographic materials, and minimal fogging. The couplers also have good fastness to light.

25 Claims, No Drawings

MATERIAL FOR COLOR PHOTOGRAPHY

In order to produce coloured photographic images, exposed silver halide emulsion layers, which at the same time contain colour couplers, are, as is known, developed with a developer substance which contains aromatic primary amino groups. The oxidised developer substance reacts with the colour coupler with the formation of an image dye, the amount of the latter depending on the amount of silver developed.

In general, a light-sensitive photographic multi-layer material is used which consists of a red-sensitive layer, which contains the cyan coupler, a green-sensitive layer, which contains the magenta coupler, and a blue-sensitive layer, which, in turn, contains the yellow coupler. On colour developing, the corresponding dyes having the colours cyan, magenta and yellow then form.

Usually, phenols or α-naphthols are employed as cyan couplers, pyrazolones are employed as magenta couplers and acylacetylamides are employed as yellow couplers. The dyes formed after developing are then indophenols, indamines or azomethines.

A structural characteristic of the conventional yellow couplers is an active methylene group, it being possible, in some cases, for one hydrogen atom to be replaced by a group which is detachable during the coupling reaction. In the first case, the couplers are termed four-equivalent couplers, since four equivalents of silver halide are required to form the image dye. In the second case, only two equivalents of silver halide are used to produce the corresponding image dye (two-equivalent couplers). These known couplers yield image dyes which each contain a chromogenic grouping (azomethine grouping) and a ballast group.

The following characteristics in particular are demanded of colour couplers which are incorporated in photographic materials: Good fastness to diffusion, i.e. no diffusion into adjacent layers. Good solubility in water or, in particular, in water-immiscible, high-boiling, organic solvents, for example tricresyl phosphate or dibutyl phthalate. Suitable absorption range and high fastness to light (no yellowing) of the dyes formed from the couplers. High reactivity of the couplers during colour formation.

Known photographic yellow couplers (such as described, for example, in German Auslegeschriften Nos. 1,116,533, 1,522,412, 1,956,281, 2,108,234 and 2,556,620, U.S. Pat. Nos. 2,500,487, 2,556,629, 2,992,920 and 3,183,095 and British Patent Specification No. 577,804) possess only some of these characteristics and it is, therefore, the object of the present invention to provide novel yellow couplers which, by reason of their reactivity, make possible accelerated processing of the photographic materials, colour developing not being disturbed by the formation of colour fogs.

The present invention relates to a light-sensitive recording material for colour photography, which contains at least one yellow coupler in at least one silver halide emulsion layer, wherein the yellow coupler has the formula

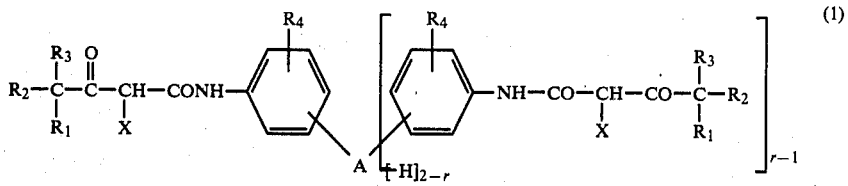

in which $R_1$ is alkyl having 1 to 18 carbon atoms, $R_2$ is alkyl having 1 to 18 carbon atoms or aryl, $R_3$ is substituted or unsubstituted alkyl, alkoxy or alkylmercapto, each having 1 to 18 carbon atoms, cycloalkylmercapto, aryl, aryloxy or arylmercapto, the sum of the carbon atoms in the substituents, $R_1$, $R_2$ and $R_3$ being 3 to 30 and at least two of these substituents being able to form a cyclic radical together with the carbon atom to which they are bonded, the $R_4$s are each halogen, alkyl, alkoxy, halogenoalkyl, alkylsulfonyl or aryloxy, X is a radical detachable during the coupling reaction, A is a 5-membered, heterocyclic, unsaturated ring system which contains 2 or 3 hetero-atoms, at least one of which is a nitrogen atom, and can be fused with a benzene ring and which is substituted by at least one ballast group and r is 1 or 2.

The recording materials for colour photography thus contain at least one yellow coupler of the formula

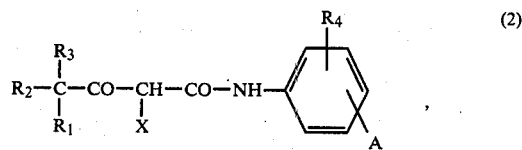

in which $R_1$, $R_2$, $R_3$, $R_4$, X and A are as defined above, or of the formula

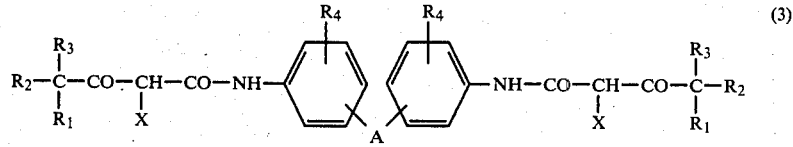

in which $R_1$, $R_2$, $R_3$, $R_4$, X and A are as defined.

The invention also relates to a process for colour photography, for the production of a yellow image by colour developing an exposed recording material which contains a compound of the formula (1) as the yellow coupler, the resulting yellow images, the compounds of the formula (1) and their preparation and the use of compounds of the formula (1) as yellow couplers in light-sensitive recording materials for colour photography.

The colour couplers employed according to the invention can thus be either 2-equivalent couplers or 4-equivalent couplers or also so-called 2×2-equivalent couplers or 2×4-equivalent couplers, i.e. compounds which possess, per molecule, two reactive positions capable of forming a colour with the oxidised developer, 2 or 4 equivalents of silver halide being consumed for each coupling position in each case.

Suitable alkyl radicals $R_1$, $R_2$ and $R_3$ in the compounds of the formula (1) can contain 1 to 18 carbon atoms and can be straight-chain or branched, for example methyl, ethyl, propyl, i-propyl, butyl, isobutyl, tert.-butyl, amyl, tert.-amyl (1,1-dimethylpropyl), 1,1,3,3-tetramethylbutyl, 1-methyl-1-ethylpentyl, hexyl, 1-methylpentyl, neopentyl, 1-, 2- or 3-methylhexyl, heptyl, n-octyl, tert.-octyl, 2-ethylhexyl, n-nonyl, isononyl, tert.-nonyl, decyl, tert.-decyl and undecyl; and also dodecyl, tetradecyl, hexadecyl and octadecyl and the corresponding isomers. Straight-chain or branched alkyl radicals having 1 to 10 carbon atoms are particularly suitable and amongst these radicals those having 1 to 4 carbon atoms are preferred, the sum of the carbon atoms in the alkyl radicals being 3 to 7. The methyl radical is particularly preferred.

Is $R_2$ aryl then it is in particular phenyl or substituted phenyl, in which substituents are halogen, for example fluorine, chlorine or bromine, or alkyl or alkoxy, preferably each having 1 to 4 carbon atoms, for example methyl, ethyl, propyl, i-propyl, butyl, tert.-butyl, methoxy, ethoxy, propoxy or butoxy, and also amino (—$NH_2$), alkylsulfonyl and acylamino; the last two radicals can be represented by the formulae —$SO_2R_9$ and —$NHCOR_{10}$, in which $R_9$ is alkyl having 1 to 5 carbon atoms, for example methyl, ethyl, propyl, i-propyl, butyl or amyl, and $R_{10}$ is likewise alkyl having 1 to 5 carbon atoms, specific radicals being the same as those mentioned for $R_9$, or is substituted or unsubstituted phenyl, in which the substituents can be the phenyl substituents mentioned.

The preferred aryl radical is phenyl substituted by halogen and alkyl or alkoxy, each having 1 to 4 carbon atoms.

If the substituent $R_3$ is alkoxy or alkylmercapto, these radicals can be straight-chain or branched and preferred radicals are those corresponding to the radicals named for alkyl. Substituents on these radicals (including alkyl) can be halogen, amino, hydroxyl or cyano. Cycloalkylmercapto $R_3$ is preferably cyclohexylmercapto. Preferred representatives of aryl, aryloxy or arylmercapto as $R_3$ are phenyl, phenoxy or phenylmercapto, which can be unsubstituted or substituted by the same substituents as those mentioned for aryl $R_2$.

Examples of cyclic radicals which can be formed by at least two of the substituents $R_1$, $R_2$ and $R_3$ together with the carbon atom to which they are bonded are mono-, di- or tri-cycloalkyl radicals having 3 to 12 carbon atoms, especially cyclopropyl, cyclobutyl, cyclopentyl and cyclohexyl, which can be substituted or unsubstituted, and also norbornyl and adamantyl.

The sum of the carbon atoms in the substituents $R_1$, $R_2$ and $R_3$ should be 3 to 30.

The substituents $R_4$, which can be identical or different from one another, are halogen, for example fluorine, bromine and especially chlorine, or also alkyl having preferably 1 to 5 carbon atoms, for example methyl, ethyl, propyl, butyl or amyl and the corresponding isomers, or also the analogous alkoxy, halogenoalkyl or alkylsulfonyl radicals. Aryloxy $R_4$ is preferably phenoxy.

Radicals X, which are detachable during the coupling reaction, are, for example, hydrogen, halogen, the radicals RO— or R'S—, in which R and R' are each alkyl, aryl, acyl or a heterocyclic radical, or 5-membered or 6-membered saturated or unsaturated heterocyclic radicals containing at least one ring nitrogen atom, by means of which they are linked to the active methine group of the yellow coupler. Bromine and in particular chlorine are suitable as detachable halogen. Alkyl R and R' can contain 1 to 4 carbon atoms; aryl is in particular phenyl, which can be substituted by nitro, carboxyl or carboxylic ester ($C_2$-$C_5$). Specific examples of carboxylic ester substituents are methyl, ethyl, propyl and butyl ester groups.

Examples of acyl radicals (R, R') are those which are derived from carboxylic acids having 2 to 5 carbon atoms, whilst with regard to the heterocyclic radicals attention is drawn to the categories of compounds indicated below.

The 5-membered or 6-membered heterocyclic radicals, which are bonded to the coupling position via a nitrogen atom, are, for example, heterocyclic radicals which contain one or more nitrogen, sulfur and/or oxygen atoms and can be fused with a further ring. Examples are the radicals of pyrazole, imidazole, the triazoles, (1,2,3 and 1,2,4) and tetrazoles, benztriazole, pyrimidine, pyridazine, thiazole, thiadiazole, oxazole and oxazine; and also cyclic imides. The said heterocyclic radicals can be in the unsubstituted or substituted form.

Attention is drawn to the following publications with regard to further details on leaving groups in two-equivalent yellow couplers: halogen atoms, as described, for example, in German Offenlegungsschrift No. 2,114,577, French Patent Specifications Nos. 991,453 and 869,169 or U.S. Pat. Nos. 2,728,658 and 3,277,155; the group —OR, in which R is alkyl, aryl, a heterocyclic radical or acyl, as described, for example, in British Patent Specification No. 1,092,506, French Patent Nos. 1,411,385 and 1,385,696 or in U.S. Pat. Nos. 3,447,928 and 3,408,194; the —SR"— group described in British Patent Specification No. 953,454 or U.S. Patent No. 3,265,506; the 1,2,3-benztriazolyl group of the formula

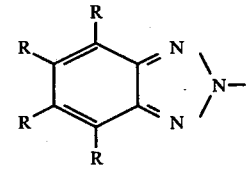

the radicals —$SO_3H$ and —SCN (British Patent Specification No. 638,039; U.S. Pat. No. 3,253,924) imide groups of the formulae

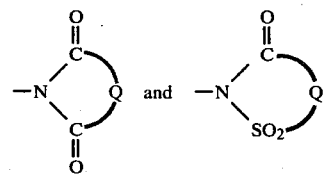

(German Offenlegungsschriften Nos. 2,163,812, 2,213,461 and 2,057,941); radicals of the formula

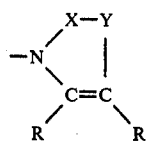

(German Offenlegungsschrift No. 2,329,587); leaving groups of the formula

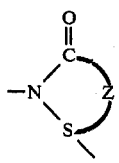

(German Offenlegungsschrift No. 2,433,812); 1,2,4-triazolyl or 1,2,3-benzotriazin-4-(3)-on-yl radicals as leaving groups (German Offenlegungsschrift No. 2,528,638); 1,2,4-triazolyl or tetrazolyl radicals as leaving groups (German Offenlegungsschrift No. 2,442,703); open-chain or cyclic sulfonamidyl radicals as leaving groups (German Offenlegungsschrift No. 2,454,741); leaving groups of the formula

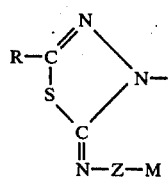

(German Offenlegungsschrift No. 2,716,204) and leaving groups of the formula

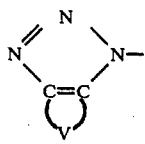

in which V together with the —C=C— grouping forms an aromatic ring of the benzene series or a heterocyclic ring containing at least one nitrogen atom (German Offenlegungsschrift No. 2,414,006).

The bridge member A (if r is 2) or the radical —A—H (if r is 1) in the compounds of the formula (1) is a 5-membered, heterocyclic, unsaturated ring system which contains 2 or 3 hetero-atoms, at least one of which is a nitrogen atom, and can be fused with a benzene ring and which is substituted by at least one ballast group. This heterocyclic ring system can contain, in the ring, for example 2 or 3 nitrogen atoms or also 1 nitrogen atom and 1 oxygen atom, 1 nitrogen atom and 1 sulfur atom, 2 nitrogen atoms and 1 oxygen atom or 2 nitrogen atoms and 1 sulfur atom. Specific ring systems are the following: diazole, triazole, oxazole, thiazole, oxadiazole, thiadiazole, diazolone, triazolone, benzoxazole, benzthiazole and benzimidazole. They can be linked via a carbon atom or atoms and/or a nitrogen atom or atoms to the adjacent phenyl ring or rings.

The heterocyclic ring systems are substituted by at least one conventional ballast group. Examples of such ballast groups are straight-chain or branched alkyl radicals having 5 to 40 carbon atoms. Straight-chain alkyl radicals can thus be, for example: pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hentriacontyl, dotriacontyl, tritriacontyl, tetratriacontyl, pentatriacontyl, hexatriacontyl, heptatriacontyl, octatriacontyl, nonatriacontyl and tetracontyl. The corresponding isomers are also suitable.

Further suitable ballast groups are the radicals listed below, in which the sum of the carbon atoms in each case should likewise be in the range of 5 to 40: alkoxy, cycloalkoxy, alkoxyalkyl, for example $CH_3(CH_2)_4$—$OCH_2$— or $CH_3O(CH_2)_5$— and homologues, alkoxycycloalkyl, for example $CH_3O(cyc)C_5H_8$— and homologues, cycloalkoxyalkyl, for example

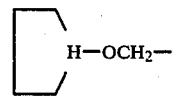

and homologues, aralkyl, for example benzyl, phenoxyalkyl, for example

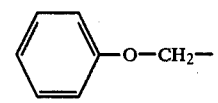

and homologues, which can be substituted by halogen (F, Cl or Br) or alkyl ($C_1$-$C_{10}$), alkyl- and dialkyl-aminoalkyl, for example $CH_3NH(CH_2)_9$—, and $C_5H_{11}NHCH_2$—,

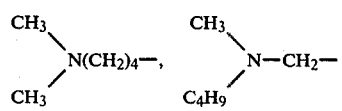

and the corresponding homologues, aryl- and diarylaminoalkyl, for example

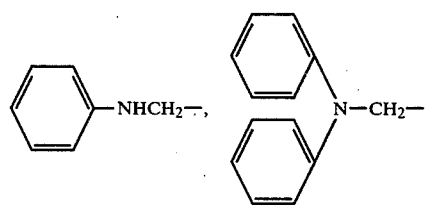

and homologues, which can be substituted in the aryl moiety by halogen (Cl, Br or I) or alkyl or alkoxy ($C_1$-$C_4$), alkylmercaptoalkyl and arylmercaptoalkyl, for example

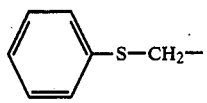

and homologues, which can be substituted as indicated for aryl- and diaryl-aminoalkyl.

Further ballast groups can be represented by the following formulae: —COOR$_{22}$, —NR$_{22}$R$_{23}$, —CONR$_{22}$R$_{23}$, —NR$_{23}$COR$_{22}$, —NR$_{23}$COR$_{24}$, —SO$_2$R$_{22}$, —SO$_2$NR$_{22}$R$_{23}$ or NR$_{23}$SO$_2$R$_{22}$, in which R$_{22}$ is alkyl having 5 to 40 carbon atoms or cycloalkyl having 5 to 12 carbon atoms, R$_{23}$ is hydrogen or alkyl having 1 to 12 carbon atoms and R$_{24}$ is alkoxy-alkyl having 5 to 20 carbon atoms or phenoxyalkyl which has 1 to 12 carbon atoms in the alkyl moiety and can be substituted on the phenyl ring by alkyl having 1 to 10 carbon atoms. Examples of alkyl are those already given above. Cycloalkyl having 5 to 12 carbon atoms is, for example, cyclopentyl, cyclooctyl or cyclododecyl and especially cyclohexyl, which, in turn, can be substituted by alkyl. The alkyl groups can contain 1 to 4 carbon atoms (methyl, ethyl, propyl, isopropyl, butyl, isobutyl or tert.-butyl) and one or more, for example two, of the alkyl substituents can be present on cyclohexyl.

The alkyl substituents (R$_{23}$) having 1 to 12 carbon atoms can be, for example, methyl, ethyl, propyl, butyl, pentyl, hexyl, heptyl, octyl, nonyl, decyl, undecyl or dodecyl or the corresponding isomers (branched alkyl).

What has been stated above applies in respect of alkoxyalkyl and phenoxyalkyl.

The heterocyclic ring systems can also contain further substituents which do not act as ballast groups, for example alkyl, alkoxy, hydroxyalkyl, halogenoalkyl (for example trifluoromethyl) or alkylmercapto, each having 1 to 4 carbon atoms, and also halogen (fluorine, chlorine or bromine), amino (—NH$_2$), hydroxyl, carbalkoxy having 1 to 4 carbon atoms in the alkoxy moiety, —CN, —CONH$_2$ and/or —NHCOR$_{21}$, in which R$_{21}$ is alkyl having 1 to 4 carbon atoms or alkoxyalkyl having 2 to 4 carbon atoms.

Preferred recording material is that which contains at least one yellow coupler of the formula

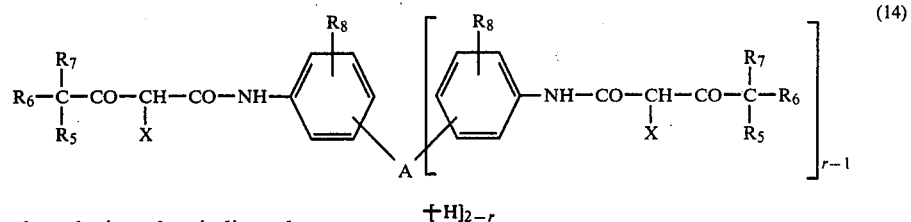

(14)

in which R$_5$ is alkyl having 1 to 10 carbon atoms, R$_6$ is alkyl having 1 to 5 carbon atoms or phenyl, which is unsubstituted or substituted by halogen, alkyl or alkoxy, each having 1 to 4 carbon atoms, —NH$_2$, —SO$_2$R$_9$ or —NHCOR$_{10}$, and R$_7$ is substituted or unsubstituted alkyl, alkoxy or alkylmercapto, each having 1 to 18 carbon atoms, cyclohexylmercapto, or phenyl, phenoxy or phenylmercapto which are unsubstituted or substituted by halogen, alkyl or alkoxy, each having 1 to 4 carbon atoms, —NH$_2$, —SO$_2$R$_9$ or —NHCOR$_{10}$, the sum of the carbon atoms in the substituents R$_5$, R$_6$ and R$_7$ being 3 to 30 and at least two of these substituents being able to form, together with the carbon atom to which they are bonded, a mono-, di- or tricycloalkyl radical having 3 to 12 carbon atoms, the R$_8$s are each halogen or alkyl, halogenoalkyl, alkoxy or alkylsulfonyl, each having 1 to 5 carbon atoms, or phenoxy, R$_9$ is alkyl having 1 to 5 carbon atoms and R$_{10}$ is alkyl having 1 to 5 carbon atoms or substituted or unsubstituted phenyl, and A, X and r are as defined.

Further recording materials which are particularly suitable are those which contain at least one yellow coupler of the formula

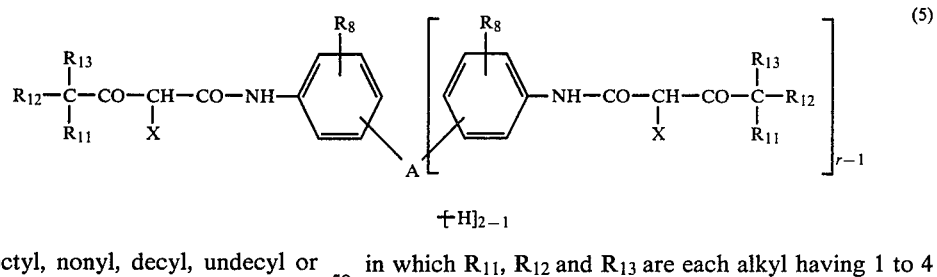

(5)

in which R$_{11}$, R$_{12}$ and R$_{13}$ are each alkyl having 1 to 4 carbon atoms, the sum of the carbon atoms in the substituents R$_{11}$, R$_{12}$ and R$_{13}$ being 3 to 7, and A, X, R$_8$ and r are as defined, or one yellow coupler of the formula

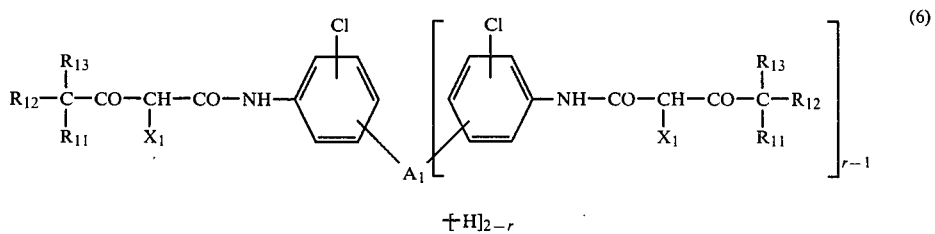

(6)

in which X$_1$ is hydrogen, halogen or the radical RO— or R'S—, in which R and R' are each alkyl, aryl, acyl or a heterocyclic radical, or X$_1$ is a heterocyclic, saturated or unsaturated radical containing at least one ring nitrogen atom, by means of which the radical is linked to the active methine group of the yellow coupler, $A_1$ is a 5-membered, heterocyclic, unsaturated ring system which contains 2 or 3 nitrogen atoms or 1 or 2 nitrogen atoms and one oxygen or sulfur atom and can be fused with a benzene ring and which is substituted by at least one ballast group, and $R_{11}$, $R_{12}$, $R_{13}$ and r are as defined.

Preferred leaving groups $X_1$ in the yellow couplers of the formula (6) are the leaving groups $X_2$ and $X_3$ as defined in the following formulae (7) and (8) for the yellow couplers present in the recording materials:

carbon atoms in the alkyl moiety, alkoxy having 1 to 18 carbon atoms or phenoxy, Y is —CO—, —SO$_2$— or —C=N—Z—M$_2$, or Y is a carbon or nitrogen atom bonded via a double bond to V, and $M_2$, if Z is —CO— or —SO$_2$—, is substituted or unsubstituted alkyl, cycloalkyl, aryl or aralkyl, or $M_2$, if Z is —CO—, is amino (NH$_2$), mono- or di-alkylamino having, in each case, 1 to 5 carbon atoms in the alkyl moiety, alkoxy having 1 to 18 carbon atoms, phenoxy, carbalkoxy having 1 to 5 carbon atoms in the alkoxy moiety, or carboxamido which is N-substituted or N,N-disubstituted by alkyl

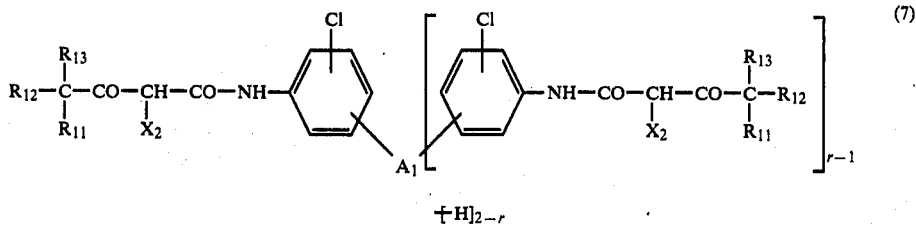
(7)

in which $X_2$ is hydrogen, halogen or a radical of the formulae having 1 to 3 carbon atoms and/or by phenyl, and V represents the nonmetallic atoms necessary to complete a 5-membered heterocyclic ring, and $R_{11}$, $R_{12}$, $R_{13}$, $A_1$ and r are as defined; and

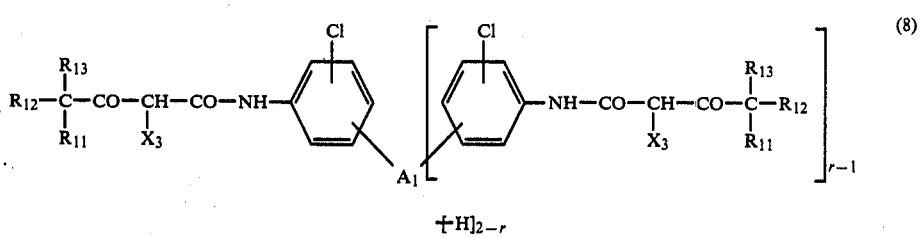
(8)

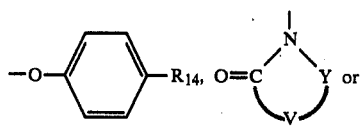

in which $X_3$ is hydrogen, chlorine, bromine or a radical of the formula

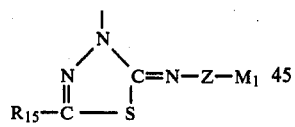

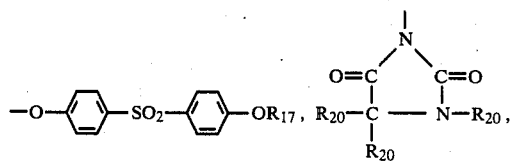

in which $R_{14}$ is —COOH, —NO$_2$, —COOR$_{16}$ or

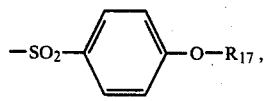

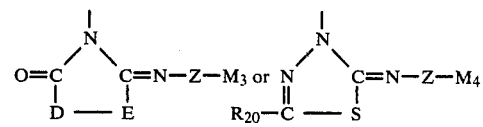

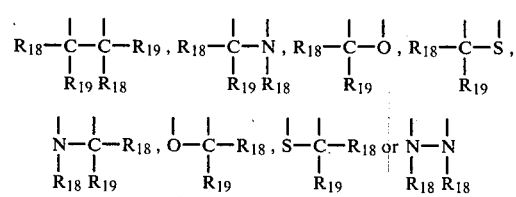

in which —D—E has the formula $R_{16}$ is alkyl having 1 to 4 carbon atoms, $R_{17}$ is alkyl having 1 to 5 carbon atoms or benzyl, $R_{15}$ is hydrogen, alkyl having 1 to 18 carbon atoms, aralkyl, aryl, pyridyl, pyrimidyl, furyl, thienyl, cycloalkyl, alkoxy having 1 to 18 carbon atoms, aryloxy, alkylmercapto having 1 to 18 carbon atoms, arylmercapto, halogen, acyl, acyloxyalkyl, trifluoromethyl, cyano, —NH$_2$, mono- or dialkylamino, each having 1 to 18 carbon atoms in the alkyl moiety, acylamino or sulfonamido, which can be N— or N,N-substituted, Z is —CO— or —SO$_2$— and $M_1$, if Z is —CO— or —SO$_2$—, is substituted or unsubstituted alkyl, cycloalkyl, aryl or aralkyl, or $M_1$, if Z is —CO—, is mono- or di-alkylamino, each having 1 to 5 in which $R_{18}$ is hydrogen, alkyl having 1 to 18 carbon atoms, aralkyl, cycloalkyl, aryl or acyl having 1 to 5 carbon atoms and $R_{19}$ is alkyl having 1 to 18 carbon atoms, aralkyl or aryl, and $R_{18}$ and $R_{19}$ together with the atom or atoms to which they are bonded can form a 4-membered to 6-membered ring, and $M_4$, if Z is —CO— or —SO$_2$—, is alkyl having 1 to 18 carbon atoms, which is unsubstituted or substituted by halogen, hydroxyl, nitro, cyano, alkoxy, aryloxy or amino, cycloalkyl having 6 to 12 carbon atoms, benzyl or phenyl, which is unsubstituted or substituted by alkyl, alkoxy or alkylmercapto, each having 1 to 5 carbon atoms, hydroxyl, nitro, cyano, amino, halogen, carboxamido, carbalkoxy, phenoxycarbonyl, benzyloxycarbonyl, —SO$_2$NH$_2$, N-substituted or N,N-disubstituted sulfonamide, acylamido or —SO$_2$G or —COG, in which G is alkyl having 1 to 18 carbon atoms, which is unsubstituted or substituted by halogen, nitro, cyano, amino or alkoxy having 1 to 18 carbon atoms, or $M_4$, if Z is —CO—, is amino, mono- or di-alkylamino having, in each case, 1 to 5 carbon atoms in the alkyl moiety, alkoxy having 1 to 18 carbon atoms, phenoxy, carbalkoxy having 1 to 5 carbon atoms in the alkoxy moiety, or carboxamido which is N-substituted or N,N-disubstituted by alkyl having 1 to 3 carbon atoms and/or by phenyl, and $M_3$, if Z is —CO— or —SO$_2$—, has the meaning defined for $M_4$, or $M_3$, if Z is —CO—, is mono- or di-alkylamino, each having 1 to 5 carbon atoms in the alkyl moiety, alkoxy having 1 to 5 carbon atoms or phenoxy, Z is —CO— or —SO$_2$—, $R_{20}$ is hydrogen, alkyl having 1 to 12 carbon atoms, benzyl, phenyl, thienyl, cycloalkyl having 6 to 12 carbon atoms, alkoxy having 1 to 5 carbon atoms, alkylmercapto having 1 to 4 carbon atoms, halogen, benzoyl, benzoyloxyalkyl having 1 to 5 carbon atoms in the alkyl moiety, benzoylamino, mono- or di-alkylsulfonamide having, in each case, 1 to 5 carbon atoms in the alkyl moiety, or —NHCOC$_n$H$_{2n+1}$, in which n is 1 to 5, and $A_1$, $R_{11}$, $R_{12}$, $R_{13}$, $R_{17}$ and r are as defined.

In the yellow couplers of the formula (8), $X_3$ is preferably hydrogen, chlorine or bromine or a radical of the formula $$-O-\langle\phantom{X}\rangle-SO_2-\langle\phantom{X}\rangle-OCH_2-\langle\phantom{X}\rangle,$$

$$\begin{array}{c} \phantom{X} \\ O=C \\ | \\ R_{20}-C \end{array} \begin{array}{c} N \\ / \\ \phantom{X} \\ | \\ \phantom{X} \end{array} \begin{array}{c} \phantom{X} \\ C=OO=C \\ | \\ N-R_{20} \end{array} \begin{array}{c} N \\ / \\ \phantom{X} \\ | \\ D \end{array} \begin{array}{c} \phantom{X} \\ C=N-Z-M_3 \\ | \\ E \end{array} \quad \text{or}$$

$$\begin{array}{c} N \\ / \\ N \\ \| \\ R_{20}-C \end{array} \begin{array}{c} \phantom{X} \\ \phantom{X} \\ \phantom{X} \\ C=N-Z-M_4 \\ | \\ S \end{array}$$

in which —D—E is as defined and the individual substituents are preferably as defined below: $R_{18}$ is hydrogen, alkyl having 1 to 5 carbon atoms, phenyl or benzyl, $R_{19}$ is alkyl having 1 to 5 carbon atoms, phenyl or benzyl, $R_{20}$ is hydrogen, alkyl having 1 to 5 carbon atoms or benzyl, $M_3$ is alkyl having 1 to 5 carbon atoms, $M_4$ is alkyl having 1 to 5 carbon atoms or phenyl, which unsubstituted or substituted by alkyl, and Z is —CO— or —SO$_2$—. The preferred radical —D—E is $$\begin{array}{c} \phantom{X} \\ R_{18}-C-N \\ | \phantom{X} | \\ R_{19}\phantom{X}R_{18} \end{array}.$$

These definitions of $X_3$ also indicate the preferred meanings in the formulae given below.

Further recording materials for colour photography which are of particular interest are those which contain at least one of the yellow couplers indicated in the following formulae (9) to (11):

$$\left[\begin{array}{c} R_{13} \\ | \\ R_{12}-C-CO-CH-CO-NH-\langle\phantom{X}\rangle-\langle\phantom{X}\rangle-NH-CO-CH-CO-C-R_{12} \\ | \phantom{XXXXXX} | \phantom{XXXXXXXXXXXXXXXXXX} | \phantom{XXXXXX} | \\ R_{11} \phantom{XXXXX} X_3 \phantom{XXXXXXXXXXXXXXXXXXXXXX} X_3 \phantom{XXXX} R_{11} \\ \phantom{XXXXXXXXXXXXXXXXX} A_2 \\ \phantom{XXXXXXXXXXXXXXX} +H]_{2-r} \end{array}\right]_{r-1} \quad (9)$$

in which $A_2$ is a diazole, triazole, oxazole, thiazole, oxadiazole, thiadiazole, diazolone, triazolone, benzoxazole, benzthiazole or benzimidazole radical with at least one ballast group and, if desired, further substituents and $R_{11}$, $R_{12}$, $R_{13}$, $X_3$ and r are as defined;

$$\begin{array}{c} R_{13} \\ | \\ R_{12}C-COCHCONH-\langle\phantom{X}\rangle \\ | \phantom{XXXX} | \\ R_{11} \phantom{XXX} X_3 \phantom{XXXXXX} A_3 \end{array} \quad (10)$$

in which $A_3$ is a benzimidazole, benzoxazole, oxadiazole, thiadiazole, diazolone, triazolone or triazole radical with at least one ballast group and, if desired, further substituents and $R_{11}$, $R_{12}$, $R_{13}$ and $X_3$ are as defined; $A_3$ is preferably a benzimidazole or oxadiazole radical; and $$\begin{array}{c} R_{13} \phantom{XXXXXXXXXXXXXXXXXXXXXXX} R_{13} \\ | \phantom{XXXXXXXXXXXXXXXXXXXXXXXXX} | \\ R_{12}-C-COCHCONH-\langle\phantom{X}\rangle-\langle\phantom{X}\rangle-NHCOCHCOC-R_{12} \\ | \phantom{XXXX} | \phantom{XXXXXXXXXXXXXXXXXX} | \phantom{XXXX} | \\ R_{11} \phantom{XXX} X_3 \phantom{XXXXXXXX} A_4 \phantom{XXXXXXX} X_3 \phantom{XX} R_{11} \end{array} \quad (11)$$

in which $A_4$ is a triazole radical with one ballast group and $R_{11}$, $R_{12}$, $R_{13}$ and $X_3$ are as defined.

The further substituents which can be present in $A_2$ and $A_3$ (formulae (9) to (10)) are, for example, alkyl, alkoxy, hydroxyalkyl, halogenoalkyl or alkylmercapto, each having 1 to 4 carbon atoms, halogen, amino, hydroxyl, carbalkoxy having 1 to 4 carbon atoms in alkoxy moiety, —CN, —CONH$_2$ and/or —NHCOR$_{21}$, in which $R_{21}$ is alkyl having 1 to 4 carbon atoms or alkoxyalkyl having 2 to 4 carbon atoms, whilst the ballast groups are alkyl, alkoxy, cycloalkoxy, alkoxyalkyl, alkoxycycloalkyl, cycloalkoxyalkyl, aralkyl, phenoxyalkyl, which can be substituted by halogen or alkyl having 1 to 10 carbon atoms, alkyl- or dialkylaminoalkyl, substituted or unsubstituted aryl- or diarylaminoalkyl, alkylmercaptoalkyl or substituted or unsubstituted arylmercaptoalkyl, in which the sum of the carbon atoms is 5 to 40 in each case; further ballast groups are —COOR$_{22}$, COR$_{22}$, —NR$_{22}$R$_{23}$, —CONR$_{22}$R$_{23}$, —NR$_{23}$COR$_{22}$, —NR$_{23}$COR$_{24}$, —SO$_2$R$_{22}$, —SO$_2$NR$_{22}$R$_{23}$ or —NR$_{25}$SO$_2$R$_{22}$, in which R$_{22}$ is alkyl having 5 to 40 carbon atoms or cycloalkyl having 5 to 12 carbon atoms, R$_{23}$ is hydrogen or alkyl having 1 to 12 carbon atoms and R$_{24}$ is alkoxyalkyl having 5 to 20 carbon atoms or phenoxyalkyl which has 1 to 12 carbon atoms in the alkyl moiety and can be substituted on the phenyl ring by alkyl having 1 to 10 carbon atoms.

Particularly preferred recording materials are those which contain at least one yellow coupler of the formula

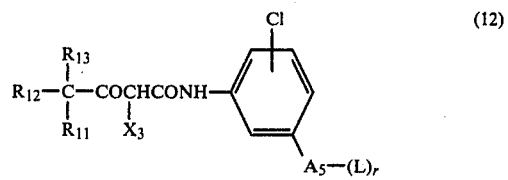

(12)

in which A$_5$ is a benzimidazole, benzoxazole, oxadiazole, thiadiazole, diazolone, triazolone or triazole radical, which can be substituted by alkyl, alkoxy and/or halogenoalkyl, each having 1 to 4 carbon atoms, or alkoxyalkyl having 2 to 4 carbon atoms, L is alkyl, alkoxy, alkoxyalkyl, phenylalkyl or phenoxyalkyl having 5 to 30 carbon atoms, —NHCOR$_{22}$ or —NR$_{23}$COR$_{24}$, in which R$_{22}$ is alkyl having 5 to 40 carbon atoms or cycloalkyl having 5 to 12 carbon atoms, R$_{23}$ is hydrogen or alkyl having 1 to 12 carbon atoms and R$_{24}$ is alkoxyalkyl having 5 to 20 carbon atoms or phenoxyalkyl which has 1 to 12 carbon atoms in the alkyl moiety and can be substituted on the phenyl ring by alkyl having 1 to 10 carbon atoms, and r is 1 or 2 and A$_3$, R$_{11}$, R$_{12}$, R$_{13}$ and X$_3$ are as defined.

Examples of the yellow couplers of the formula (12) have, in particular, the following formula (13) to (15):

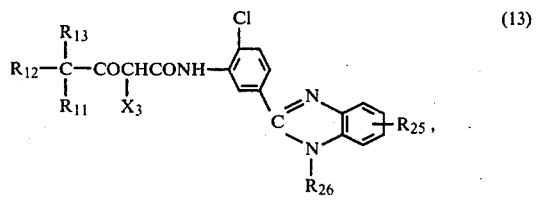

(13)

in which R$_{25}$ is hydrogen or alkyl, alkoxy and/or halogenoalkyl, each having 1 to 4 carbon atoms, and R$_{26}$ is alkyl, alkoxyalkyl, phenylalkyl or phenoxyalkyl having 8 to 30 carbon atoms and R$_{11}$, R$_{12}$, R$_{13}$ and X$_3$ are as defined,

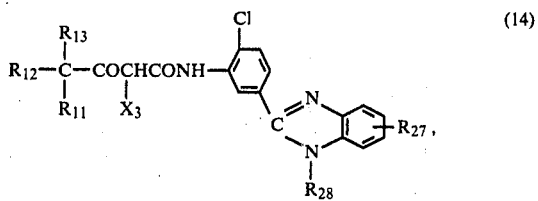

(14)

in which R$_{27}$ is alkyl, alkoxy, alkoxyalkyl, phenylalkyl or phenoxyalkyl having 8 to 30 carbon atoms, —NR$_{23}$COR$_{22}$ or —NR$_{23}$COR$_{24}$, R$_{22}$ is alkyl having 5 to 40 carbon atoms or cycloalkyl having 5 to 12 carbon atoms, R$_{23}$ is hydrogen or alkyl having 1 to 12 carbon atoms, R$_{24}$ is alkoxyalkyl having 5 to 20 carbon atoms or phenoxyalkyl which has 1 to 12 carbon atoms in the alkyl moiety and can be substituted on the phenyl ring by alkyl having 1 to 10 carbon atoms, and R$_{28}$ is hydrogen or alkyl or halogenoalkyl, each having 1 to 4 carbon atoms, and R$_{11}$, R$_{12}$, R$_{13}$ and X$_3$ are as defined, and

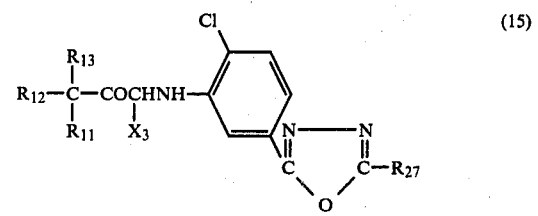

(15)

in which R$_{27}$ is alkyl, alkoxyalkyl, phenylalkyl or phenoxyalkyl having 8 to 30 carbon atoms, —NR$_{23}$COR$_{22}$ or —NR$_{23}$COR$_{24}$, R$_{22}$ is alkyl having 5 to 40 carbon atoms or cycloalkyl having 5 to 12 carbon atoms, R$_{23}$ is hydrogen or alkyl having 1 to 12 carbon atoms, R$_{24}$ is alkoxyalkyl having 5 to 20 carbon atoms or phenoxyalkyl which has 1 to 12 carbon atoms in the alkyl moiety and can be substituted on the phenyl ring by alkyl having 1 to 10 carbon atoms, and R$_{11}$, R$_{12}$, R$_{13}$ and X$_3$ are as defined.

In the formulae (13) to (15), R$_{11}$, R$_{12}$ and R$_{13}$ are in particular methyl and R$_{26}$ and R$_{27}$ are each alkyl having 8 to 30 carbon atoms.

Specific examples of yellow couplers are those given below, the use of which in the recording materials according to the invention leads to particularly advantageous results:

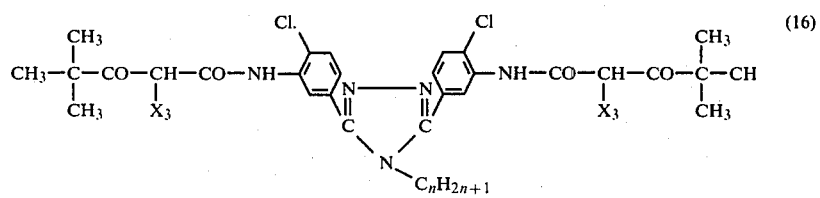

(16)

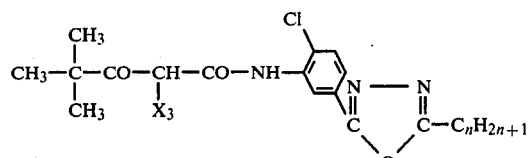

(17)

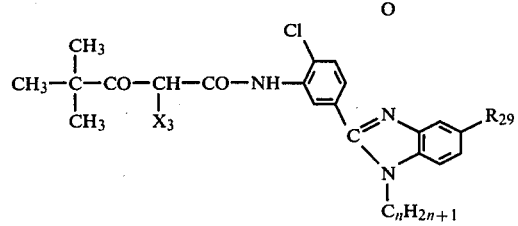

(18)

in which n is 8 to 25 and $R_{29}$ is hydrogen, methoxy or trifluoromethyl and $X_3$ is as defined.

The yellow couplers of the formulae (1) to (18) can be prepared in accordance with the following reaction equation:

by replacing the halogen atom (Hal) by known methods. The heterocyclic compounds substituted by a nitrophenyl radical are prepared by known methods which have been described in the literature. The preparation of such compounds is described, for example, in Chem. Ber. 26, 427 (1893) and 93,2,108 (1960), German Auslegeschrift No. 1,670,914 and British Patent Specification No. 970,480. Aminobenzimidazoles are prepared direct in situ from substituted or unsubstituted N-(nitrobenzoyl)-2-nitroanilines, by reduction and cyclisation. The reduction of the nitro compounds is generally effected with iron powder in ethanol in the presence of hydrochloric acid (Bechamp process).

The reaction of the aniline containing heterocyclic substituents with the acylacetic acid ester is effected by the process known from U.S. Pat. No. 3,265,506. With regard to the acylacetic acid esters, attention is drawn to British Patent Specification No. 980,507 and German Offenlegungsschriften Nos. 1,124,356, 1,956,281, 2,503,099 and 2,514,314.

Examples of anilines containing heterocyclic substitu-

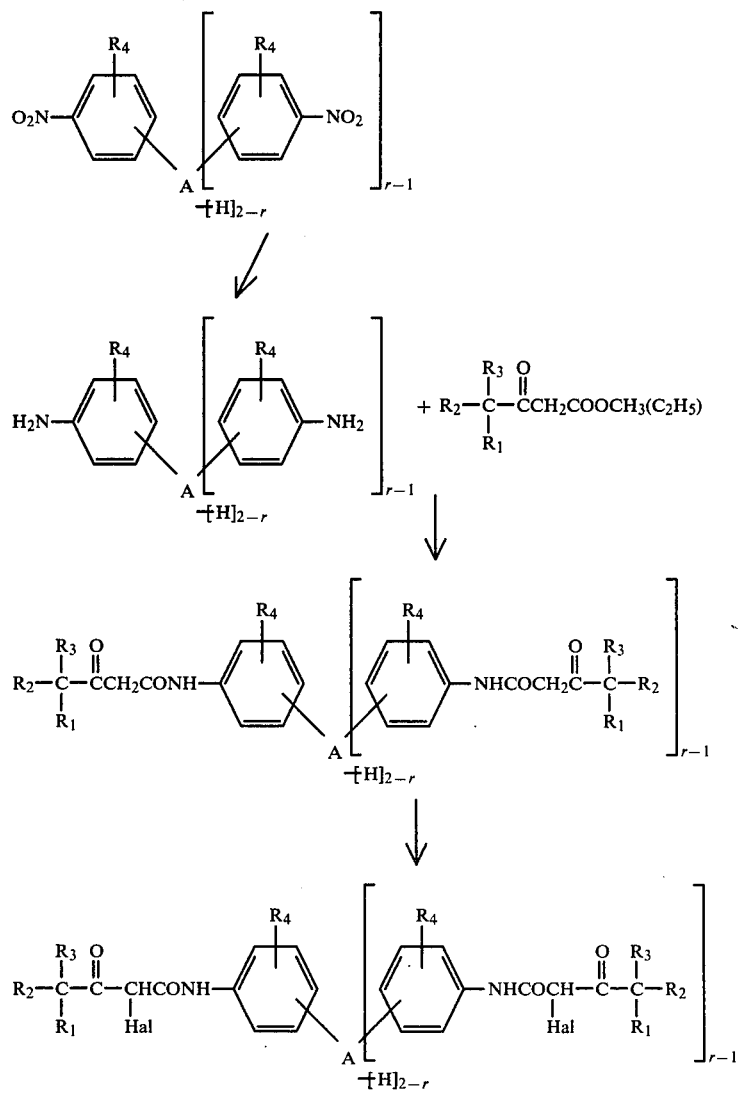

The other leaving groups (radicals which are detachable during the coupling reaction and are neither hydrogen nor halogen) can be introduced into the molecule ents and of acylacetic acid esters which can be employed are the compounds named below:

1. 6-n-Dodecyl-2-(4'-aminophenyl)-benzthiazole,
2. 2-(3'-Aminophenyl)-5-myristylamino-benzoxazole,
3. 2-(3'-Amino-4'-chloro-phenyl)-5-stearylamino-benzoxazole,
4. 3-(4'-Aminophenyl)-4-dodecyl-1-methyl-1,2,4-triazolone,
5. 3-Hexadecyl-5-(3'-amino-4'-methyl-phenyl)-1,2,4-oxadiazole,
6. 1-(4'-Aminophenyl)-3-decyl-1,2,4-triazole,
7. 3-(3'-Amino-4'-methyl-phenyl)-1-ethyl-4-hexyl-1,2,4-triazol-5-one,
8. 3-Dodecyl-5-(4'-aminophenyl)-1,2,4-oxadiazole,
9. 2-(3'-Amino-4'-chloro-phenyl)-3-dodecyl-4,5-dimethylimidazole,
10. 2-(4'-Aminophenyl)-4-dodecyl-thiazole,
11. 1-(4'-Amino-3'-methoxy-phenyl)-3-octyl-1,2,4-triazole.
12. 5-(4'-Aminophenyl)-3-[α-(3'-t-butyl-4'-hydroxyphenoxy)butyramino]-1,3,4-thiadiazole,
13. 2-(3'-Aminophenyl)-4-tetradecyl-thiazole,
14. 5-(3'-Amino-4'-methyl-phenyl)-3-stearylamino-1,3,4-thiadiazole,
15. 1-Hexadecyl-2-(3'-amino-4'-chloro-phenyl)-benzimidazole,
16. 1-Decyl-2-(4'-aminophenyl)-benzimidazole,
17. 1-Dodecyl-6-trifluoromethyl-2-(3'-amino-4'-chlorophenyl)-benzimidazole,
18. 6-Ethoxy-1-octyl-2-(3'-amino-4'-methyl-phenyl)benzimidazole,
19. 1-Hexadecyl-6-methylsulfonyl-2-(3'-amino-4'-methoxyphenyl)-benzimidazole.
1. Methyl 4,4-dimethyl-3-oxo-valerate,
2. Methyl 4-methoxy-4-methyl-3-oxo-valerate,
3. Methyl 4-methyl-4-phenoxy-3-oxo-valerate,
4. Methyl 4,4-dimethyl-3-oxo-caproate,
5. Methyl 4,4-dimethyl-3-oxo-arachate,
6. Ethyl 4-ethyl-4-methyl-3-oxo-caprylate,
7. Methyl 4,4,6,6-tetramethyl-3-oxo-enanthate,
8. Methyl 3-(1'-methyl-cyclohexyl)-3-oxo-propionate,
9. Methyl 3-(7',7'-dimethylnorbornyl-1)-3-oxo-propionate,
10. Methyl 4-methylthio-4-methyl-3-oxo-valerate,
11. Methyl 4-phenylthio-4-methyl-3-oxo-valerate,
12. Methyl 4-methyl-4-phenyl-3-oxo-valerate,
13. Methyl 4,4-diphenyl-3-oxo-valerate.

The yellow couplers according to the invention are a category of compounds which is novel per se. Compared with yellow couplers which have the same leaving groups but different ballast groups, they are distinguished by high reactivity (high maximum density), which makes possible accelerated processing of the photographic materials, and minimal fogging. The couplers also have good fastness to light. Moreover, the yellow dyes which are formed on colour development have excellent fastness to light, moisture, printing and heat, have no undesired secondary absorptions in the long wavelength range and give a colour shade which is exceptionally advantageous for colour reproduction.

The colour couplers of the formulae (1) to (18), which are also a subject of the present invention, can be incorporated in a known manner into photographic layers, for example into silver halide emulsions containing gelatine and/or other binders.

For example, they can be used in silver bromide, silver chloride or silver iodide emulsions or in those emulsions which contain a mixture of silver halides, such as silver bromide/iodide or silver chloride/bromide emulsions.

The emulsions can be chemically sensitised and they can also contain conventional organic stabilisers and anti-fogging agents, as well as conventional plasticisers, for example glycerol. The emulsions can also be hardened with the hardeners customary for gelatine. Furthermore, the emulsions can contain conventional coating aids. The emulsions can be applied to conventional layer supports for recording material for photography. If desired, a mixture of several colloids can be used to disperse the silver halides.

The conventional developing baths can be employed for developing the recording material for colour photography. These baths as a rule contain a developer substance of the p-phenylenediamine type, a development retarder, such as potassium bromide, an antioxidant, such as sodium sulfite, and a base, for example an alkali metal hydroxide or alkali metal carbonate. Furthermore, the developing baths can contain a conventional anti-fogging agent and complexing agents.

Corresponding application possibilities are described, for example, in U.S. Pat. Nos. 2,304,939, 2,304,940, 2,322,027, 2,284,879, 2,801,170, 2,801,171, 2,749,360 and 2,825,382.

In the following examples parts and percentages are by weight.

EXAMPLE 1

(a)

N-(4-Chloro-3-nitro-benzoyl)-N-n-hexadecyl-2-nitroaniline

A solution of 33 g of 4-chloro-3-nitro-benzoyl chloride in 100 ml of benzene is added dropwise in the course of one hour to a solution, which has been heated to the reflux temperature, of 54.3 g of N-n-hexadecyl-2-nitroaniline in 80 ml of benzene. After a further two hours, the reaction has ended. The reaction solution is poured into 600 ml of hexane and the mixture is left to stand overnight. The resulting crystals are filtered off with suction and washed with hexane. This gives 48 g of the compound with a melting point of 83° to 85° C.

(b)

2-(4'-Chloro-3'-aminophenyl)-1-n-hexadecyl-benzimidazole

A solution of 42 g of N-(4-chloro-3-nitrobenzoyl)N-n-hexadecyl-2-nitro-aniline in 700 ml of ethanol is allowed to run rapidly into a mixture, which has been heated to 60° C., of 89 g of iron powder in 120 ml of water and 40 ml of concentrated hydrochloric acid, with vigorous stirring. The reaction mixture is then stirred for four hours at the reflux temperature. A further 100 ml of concentrated hydrochloric acid and 200 ml of ethanol are then added and the mixture is filtered hot. About 400 ml of ethanol are then distilled off and the residue is left to crystallise out at 4° C. After filtering and drying, 32 g of the compound are obtained in the form of the hydrochloride with a melting point of 162° to 163° C.

(c)

3 g of compound (b) are added to a mixture of 15 ml of xylene and 10 ml of 2 normal aqueous sodium carbonate solution, the mixture is shaken until the solid material has dissolved, the xylene phase is separated off, washed with a little water and filtered and about half of the xylene is distilled off. 1.8 g of methyl pivaloylacetate are added to the residual solution, the mixture is then heated to 150° C. and the methyl alcohol formed is distilled off. Xylene and excess pivaloyl-acetate are then distilled off in vacuo and the residue is purified by chromatography in a column containing 40 g of silica gel (solvent system benzene/ethyl acetate: 17:3). 1.4 g of the coupler of the formula (101) are obtained in the form of a yellowish powder with a melting point of 70° to 72° C.

The couplers of the formulae (102) to (105) in Table 1, which is given below, are also prepared analogously.

EXAMPLE 2

A solution of 3.4 g of sulfuryl chloride in 20 ml of toluene is added dropwise in the course of 10 minutes, at 0° C., to a solution of 12 g of the coupler of the formula (102) in 70 ml of toluene, with good stirring. The mixture is allowed to react further for one hour more at room temperature, 60 ml of water are added and the mixture is neutralised with 2 normal aqueous sodium carbonate solution. The toluene solution is separated off and filtered and the filtrate is evaporated in vacuo. After recrystallisation of the residue from ether, the coupler of the formula (106) is obtained in the form of a white powder with a melting point of 144° to 147° C.

The couplers of the formulae (107) to (109) in Table 1, which is given below, are prepared analogously.

EXAMPLE 3

A solution of 0.8 g of bromine in 10 ml of chloroform is added dropwise in the course of two hours, at 0° to 2° C., to a solution of 3.3 g of 2-chloro-5-(3'-n-hexadecyl-6'-trifluoromethyl-benzimidazol-2-yl)-pivaloylacetanilide in 30 ml of chloroform, with vigorous stirring. After adding 20 ml of water, the mixture is neutralised with 2 normal aqueous sodium carbonate solution, the chloroform solution is separated off and filtered and the filtrate is evaporated to dryness in vacuo. After recrystallisation of the residue from hexane, the coupler of the formula (110) is obtained in the form of a white powder with a melting point of 75° to 76° C.

EXAMPLE 4

0.23 g of finely powdered potassium hydroxide is added to a solution of 1 g of 5-isopropyl-2-toluenesulfonylimino-3H-1,3,4-thiadiazoline in 25 ml of acetonitrile and the mixture is stirred for about 30 minutes at room temperature. 1.4 g of the coupler of the formula (109) are then added and the mixture is stirred, first for 2 hours at room temperature and then for 2 hours at 40° C. After filtering and removing the acetonitrile, the product is purified by chromatography through a column containing silica gel and is recrystallised from petroleum ether. 1.4 g of the coupler of the formula (111) are obtained in the form of a white powder with a melting point of 90° to 94° C.

The couplers of the formulae (112) to (118) in Table 1, which is given below, are prepared analogously.

TABLE 1

Yellow couplers of the formula (100)

(CH$_3$)$_3$CCOCHCONH—[Cl-substituted phenyl with A]
             |
             X

| No. | X | A | Melting Point °C. |
|---|---|---|---|
| (101) | H | 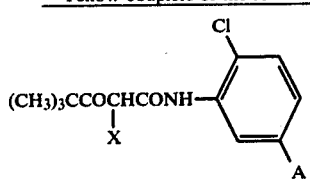 n-C$_{16}$H$_{33}$ | 70–72 |
| (102) | H | 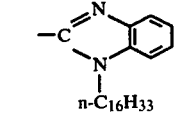 CH$_2$CH(CH$_2$)$_3$CH$_3$ / C$_2$H$_5$ | 121–123 |
| (103) | H | 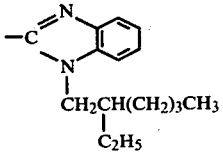 OCH$_3$ / n-C$_{16}$H$_{33}$ | 25–27 |
| (104) | H | 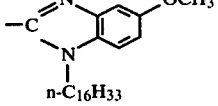 n-C$_{10}$H$_{21}$ | 86–88 |
| (105) | H | 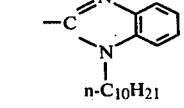 —C$_{17}$H$_{35}$(n) | 84–87 |

TABLE 1-continued

Yellow couplers of the formula $$(CH_3)_3CCOCHCONH-\underset{X}{\overset{Cl}{\underset{A}{\bigcirc}}} \quad (100)$$

| No. | X | A | Melting Point °C. |
|---|---|---|---|
| (106) | Cl | (quinazoline with N-CH$_2$CH(C$_2$H$_5$)(CH$_2$)$_3$CH$_3$) | 144–147 |
| (107) | Cl | (quinazoline with N-n-C$_{16}$H$_{33}$) | 58–59 |
| (108) | Cl | (quinazoline with N-CH$_3$ and -NHCOCH$_2$O-phenyl-2,4-di(t)C$_5$H$_{11}$) | 160–164 |
| (109) | Cl | (oxadiazole with -C$_{17}$H$_{35}$(n)) | 72–74 |
| (110) | Br | (quinazoline with CF$_3$, N-n-C$_{16}$H$_{33}$) | 75–76 |
| (111) | (thiadiazoline-N(CH(CH$_3$)$_2$)=NSO$_2$-C$_6$H$_4$-CH$_3$) | (oxadiazole with -C$_{17}$H$_{35}$(n)) | 90–94 |
| (112) | (hydantoin with CH$_2$-phenyl) | (quinazoline with N-n-C$_{16}$H$_{33}$) | 62–65 |
| (113) | (hydantoin with =NCOC(CH$_3$)$_3$, diphenyl, NH) | (quinazoline with N-n-C$_{16}$H$_{33}$) | 160–161 |
| (114) | (thiadiazoline-CH(CH$_3$)$_2$, -NSO$_2$-C$_6$H$_4$-CH$_3$) | (quinazoline with N-n-C$_{16}$H$_{33}$) | 85–89 |

TABLE 1-continued

Yellow couplers of the formula (100)

$$(CH_3)_3CCOCOCHCONH-\underset{X}{\overset{Cl}{\bigcirc}}-A$$

| No. | X | A | Melting Point °C. |
|---|---|---|---|
| (115) | [N-substituted imidazolinone with two phenyl groups, NH, and C=NCOC(CH₃)₃] | quinazoline-type with $-CH_2CH(CH_2)_3CH_3$ / $C_2H_5$ | 223–226 |
| (116) | $-O-\bigcirc-SO_2-\bigcirc-OCH_2-\bigcirc$ | quinazoline with $CF_3$, $n\text{-}C_{16}H_{33}$ | 82–86 |
| (117) | [imidazolinone with two phenyl, NH, C=NCOC(CH₃)₃] | quinazoline with $CF_3$, $n\text{-}C_{16}H_{33}$ | 65–67 |
| (118) | [triazole with $-SCH_3$] | quinazoline with $CF_3$, $n\text{-}C_{16}H_{33}$ | Resin |

EXAMPLE 5

A solution of 12 g of 3,5-bis-(4-chloro-3-nitrophenyl)-4-n-hexadecyl-1,2,4-triazole (prepared in accordance with British Patent Specification No. 970,480) in a mixture of 30 ml of dimethylformamide and 60 ml of ethanol is added to a mixture of 20 g of iron powder, 20 ml of glacial acetic acid, 2 ml of concentrated hydrochloric acid and 3 ml of water, with stirring. The reaction mixture is stirred at 50° to 55° C. for 30 minutes. After adding a further 100 ml of ethanol, the mixture is filtered and the filtrate is evaporated in vacuo. The residue is dissolved in about 30 ml of dimethylformamide and this solution is added dropwise to about one liter of water, with good stirring. The resulting precipitate is filtered off, washed with water and dried in vacuo. This gives 10.2 g of 3,5-bis-(3-amino-4-chlorophenyl)-4-n-hexadecyl-1,2,4-triazole with a melting point of 88° to 90° C.

3 g of the compound thus obtained are heated together with 10 g of methyl pivaloylacetate in 10 ml of p-xylene for a total of 14 hours at 150° C. The solvent and the excess ester are then distilled off in vacuo and the residue is separated by chromatography through a column containing silica gel. The coupler of the formula (201) is obtained in the form of a pale beige powder with a melting point of 50° to 51° C.

The coupler of the formula (202) is prepared analogously to the process according to Example 2 and the couplers of the formulae (203) to (205) are prepared analogously to the process according to Example 4. The formulae are given in Table 2 below.

TABLE 2

Yellow couplers of the formula (200)

$$(CH_3)_3CCOCHCONH-\underset{X}{\bigcirc}\overset{Cl}{-}\underset{N}{\overset{}{\bigcirc}}\cdots\underset{n\text{-}C_{16}H_{33}}{\overset{}{\bigcirc}}\cdots\underset{}{\overset{Cl}{\bigcirc}}-NHCOCHCOC(CH_3)_3$$

| No. | X | Melting point °C. |
|---|---|---|
| (201) | —H | 50–57 |

TABLE 2-continued

Yellow couplers of the formula (CH₃)₃CCOCHCONH—[Cl-phenyl]—N=C—N(n-C₁₆H₃₃)—C=N—[Cl-phenyl]—NHCOCHCOC(CH₃)₃ with X substituents (200)

| No. | X | Melting point °C. |
|---|---|---|
| (202) | —Cl | 75–82 |
| (203) | N-succinimide with CH₂—NCH₂—phenyl | 93–97° |
| (204) | O=C—N—C=NCOC(CH₃)₃ ring with diphenyl-C | 124–129° |
| (205) | N=N—C(CH(CH₃)₂)—S—C=NSO₂—C₆H₄—CH₃ | 95–100° |

EXAMPLE 6

In each case 0.1 mmol of yellow coupler is dissolved in 2.0 ml of tricresyl phospate/methylene chloride (1:9). The methylene chloride is evaporated off, 2.0 ml of an 8% aqueous solution of sodium isopropylnaphthalene-sulfonate, 6.6 ml of 6% gelatine solution and 1.2 ml of water are added, the pH of the mixture is adjusted to 6.5 and the mixture is emulsified for 5 minutes with the aid of an ultrasonic device with an output of 100 watts.

2.5 ml of the coupler emulsion, freshly exposed to ultrasonic waves, X . 0.4 ml of silver bromide emulsion, where X is the number of stoichiometric equivalents of silver per mol of coupler, which has a pH of 6.5 and contains 1.4% of silver and 6.0% of gelatine, 1.0 ml of a 1% aqueous solution of the hardener of the formula

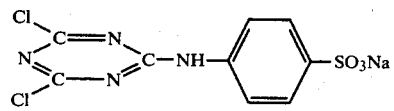

and 5.0 ml of water are mixed together and coated, at 40° C., onto a subbed 13 cm×18 cm glass plate.

After the mixture has solidified at 10° C., the plate is dried in a circulating air drying cabinet at room temperature.

A strip cut to 4.0 cm×6.5 cm is exposed, at 500 Lux, under a step wedge for 2 seconds and then treated at 24° C. as follows:

| | minutes |
|---|---|
| 1. Colour development | 5 |
| 2. Washing | 5 |
| 3. First fixing | 2 |
| 4. Washing | 2 |
| 5. Silver bleaching | 4 |
| 6. Washing | 2 |
| 7. Second fixing | 4 |
| 8. Washing | 10 |
| 9. Drying | 10 |

A colour developer of the following composition is used for processing:

| | |
|---|---|
| 4-Amino-3-methyl-N-ethyl-N-[β-(methyl-sulfonamido)-ethyl]-aniline . 1½ H₂SO₄ . H₂O | 10 mmol/l |
| Anhydrous sodium sulfite | 2.0 g/l |
| Potassium bromide | 0.5 g/l |
| Potassium carbonate | 40.0 g/l |
| Benzyl alcohol | 10.0 ml/l |
| (pH : 10.7) | |

Conventional baths are used for fixing and silver bleaching.

The maximum density and the absorption maximum of the step wedge thus obtained are measured. The values given in Table 3 are obtained.

TABLE 3

| Coupler of the formula | λmax | D$_{max}$ |
|---|---|---|
| 101 | 446 nm | 1.15 |
| 102 | 449 nm | 1.40 |
| 103 | 448 nm | 1.44 |

TABLE 3-continued

| Coupler of the formula | λmax | $D_{max}$ |
|---|---|---|
| 104 | 449 nm | 1.40 |
| 105 | 448 nm | 1.37 |
| 106 | 449 nm | 1.53 |
| 108 | 449 nm | 1.12 |
| 109 | 449 nm | 1.26 |
| 111 | 449 nm | 1.59 |
| 112 | 448 nm | 1.40 |
| 113 | 448 nm | 1.24 |
| 114 | 447 nm | 1.38 |
| 115 | 449 nm | 1.32 |
| 116 | 448 nm | 1.54 |
| 117 | 448 nm | 1.24 |

What is claimed is:

1. A light-sensitive recording material for colour photography, which contains at least one yellow coupler in at least one silver halide emulsion layer, wherein the yellow coupler has the formula

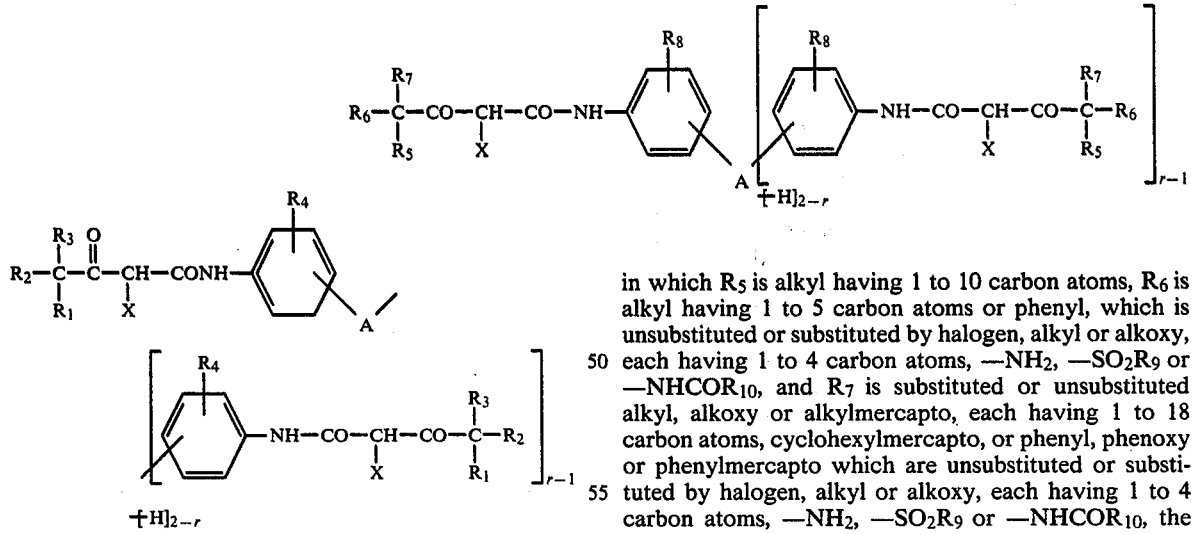

in which $R_1$ is alkyl having 1 to 18 carbon atoms, $R_2$ is alkyl having 1 to 18 carbon atoms or aryl, $R_3$ is substituted or unsubstituted alkyl, alkoxy or alkylmercapto, each having 1 to 18 carbon atoms, cycloalkylmercapto, aryl, aryloxy or arylmercapto, the sum of the carbon atoms in the substituents $R_1$, $R_2$ and $R_3$ being 3 to 30 and at least two of these substituents being able to form a cyclic radical together with the carbon atom to which they are bonded, the $R_4$s are each halogen, alkyl, alkoxy, halogenoalkyl, alkylsulfonyl or aryloxy, X is a radical detachable during the coupling reaction, A is a 5-membered, heterocyclic, unsaturated ring system which contains 2 or 3 hetero-atoms, at least one of which is a nitrogen atom, and can be fused with a benzene ring and which is substituted by at least one ballast group and r is 1 or 2.

2. A recording material according to claim 1, wherein the yellow coupler has the formula

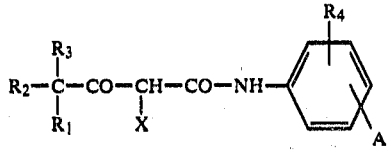

in which $R_1$, $R_2$, $R_3$, $R_4$, X an A are as defined in claim 1.

3. A recording material according to claim 1, wherein the yellow coupler has the formula

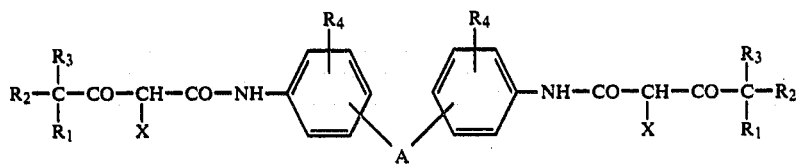

in which $R_1$, $R_2$, $R_3$, $R_4$, X and A are as defined in claim 1.

4. A recording material according to claim 1, wherein the yellow coupler has the formula in which $R_5$ is alkyl having 1 to 10 carbon atoms, $R_6$ is alkyl having 1 to 5 carbon atoms or phenyl, which is unsubstituted or substituted by halogen, alkyl or alkoxy, each having 1 to 4 carbon atoms, —$NH_2$, —$SO_2R_9$ or —$NHCOR_{10}$, and $R_7$ is substituted or unsubstituted alkyl, alkoxy or alkylmercapto, each having 1 to 18 carbon atoms, cyclohexylmercapto, or phenyl, phenoxy or phenylmercapto which are unsubstituted or substituted by halogen, alkyl or alkoxy, each having 1 to 4 carbon atoms, —$NH_2$, —$SO_2R_9$ or —$NHCOR_{10}$, the sum of the carbon atoms in the substituents $R_5$, $R_6$ and $R_7$ being 3 to 30 and at least two of these substituents being able to form, together with the carbon atom to which they are bonded, a mono-, di- or tricycloalkyl radical having 3 to 12 carbon atoms, the $R_8$s are each halogen or alkyl, halogenoalkyl, alkoxy or alkylsulfonyl, each having 1 to 5 carbon atoms, or phenoxy, $R_9$ is alkyl having 1 to 5 carbon atoms and $R_{10}$ is alkyl having 1 to 5 carbon atoms or substituted or unsubstituted phenyl, and A, X and r are as defined in claim 1.

5. A recording material according to claim 4, wherein the yellow coupler has the formula

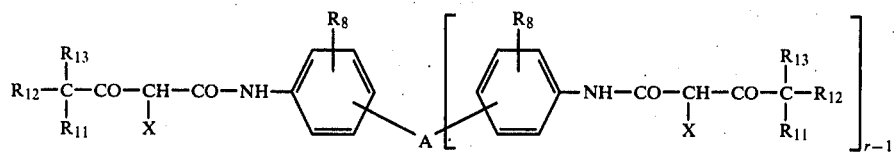

$[H]_{2-1}$ in which $R_{11}$, $R_{12}$ and $R_{13}$ are each alkyl having 1 to 4 carbon atoms, the sum of the carbon atoms in the substituents $R_{11}$, $R_{12}$ and $R_{13}$ being 3 to 7, and A, X, $R_8$ and r are as defined in claim 4.

6. A recording material according to claim 5, wherein the yellow coupler has the formula

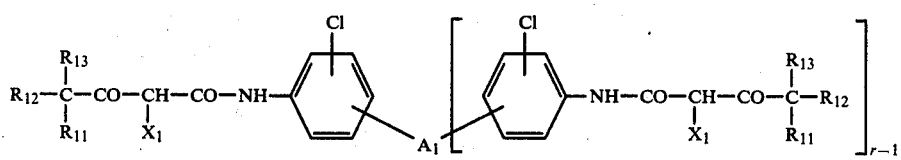

$[H]_{2-r}$ in which $X_1$ is hydrogen, halogen or the radical RO— or R'S—, in which R and R' are each alkyl, aryl, acyl or a heterocyclic radical, or $X_1$ is a heterocyclic, saturated or unsaturated radical containing at least one ring nitrogen atom, by means of which the radical is linked to the active methine group of the yellow coupler, $A_1$ is a 5-membered, heterocyclic, unsaturated ring system which contains 2 or 3 nitrogen atoms or 1 or 2 nitrogen atoms and one oxygen or sulfur atom and can be fused with a benzene ring and which is substituted by at least one ballast group, and $R_{11}$, $R_{12}$, $R_{13}$ and r are as defined in claim 5.

7. A recording material according to claim 6, wherein the yellow coupler has the formula

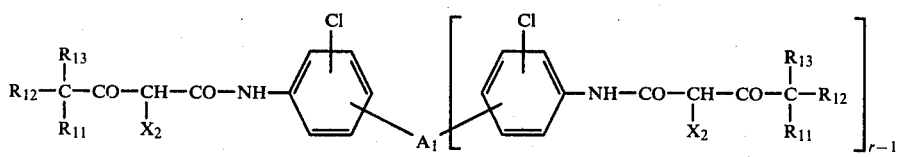

$[H]_{2-r}$ in which $X_2$ is hydrogen, halogen or a radical of the formulae

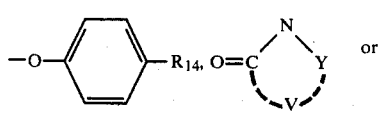 or

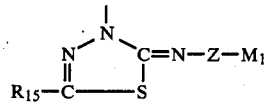

in which $R_{14}$ is —COOH, —NO$_2$, —COOR$_{16}$ or

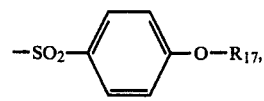

$R_{16}$ is alkyl having 1 to 4 carbon atoms, $R_{17}$ is alkyl having 1 to 5 carbon atoms or benzyl, $R_{15}$ is hydrogen, alkyl having 1 to 18 carbon atoms, aralkyl, aryl, pyridyl, pyrimidyl, furyl, thienyl, cycloalkyl, alkoxy having 1 to 18 carbon atoms, aryloxy, alkylmercapto having 1 to 18 carbon atoms, arylmercapto, halogen, acyl, acyloxyalkyl, trifluoromethyl, cyano, —NH$_2$, mono- or di-alkylamino, each having 1 to 18 carbon atoms in the alkyl moiety, acylamino or sulfonamide, which can be N— or N,N-substituted, Z is —CO— or —SO$_2$— and M$_1$, if Z is —CO— or —SO$_2$—, is substituted or unsubstituted alkyl, cycloalkyl, aryl or aralkyl, or M$_1$, if Z is —CO—, is mono- or di-alklamino, each having 1 to 5 carbon atoms in the alkyl moiety, alkoxy having 1 to 18 carbon atoms or phenoxy, Y is —CO—, —SO$_2$— or —C=N—Z—M$_2$, or Y is a carbon or nitrogen atom bonded via a double bond to V, and M$_2$, if Z is —CO— or —SO$_2$—, is substituted or unsubstituted alkyl, cycloalkyl, aryl or aralkyl, or $M_2$, if Z is —CO—, is amino ($NH_2$), mono- or di-alkylamino having, in each case, 1 to 5 carbon atoms in the alkyl moiety, alkoxy having 1 to 18 carbon atoms, phenoxy, carbalkoxy having 1 to 5 carbon atoms in the alkoxy moiety, or carboxamido which is N-substituted or N,N-disubstituted by alkyl having 1 to 3 carbon atoms and/or by phenyl, and V represents the non-metallic atoms necessary to complete a 5-membered heterocyclic ring, and $R_{11}$, $R_{12}$, $R_{13}$, $A_1$ and r are as defined in claim 6.

8. A recording material according to claim 7, wherein the yellow coupler has the formula

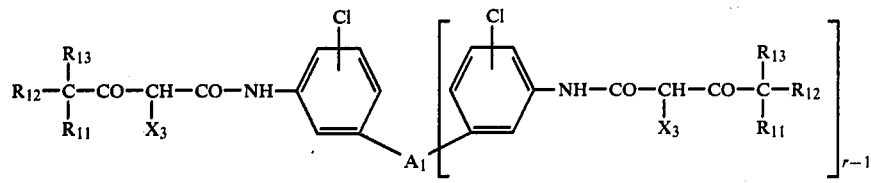

in which $X_3$ is hydrogen, chlorine, bromine or a radical of the formula

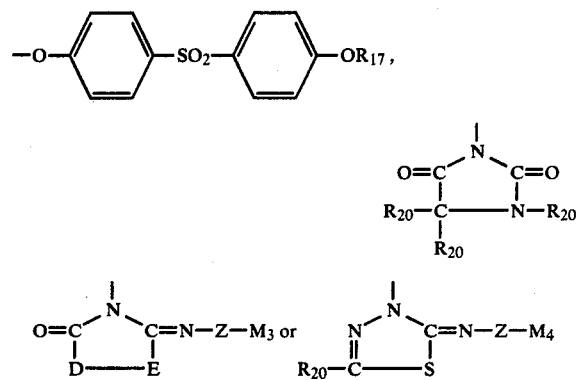

in which —D—E has the formula

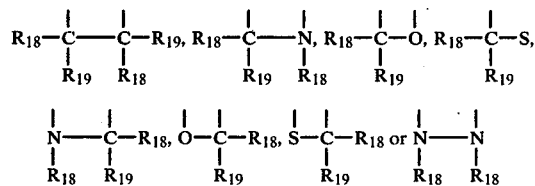

in which $R_{18}$ is hydrogen, alkyl having 1 to 18 carbon atoms, aralkyl, cycloalkyl, aryl or acyl having 1 to 5 carbon atoms, and $R_{19}$ is alkyl having 1 to 18 carbon atoms, aralkyl or aryl, and $R_{18}$ and $R_{19}$ together with the atom or atoms to which they are bonded can form a 4-membered to 6-membered ring, and $M_4$, if Z is —CO— or —$SO_2$—, is alkyl having 1 to 18 carbon atoms, which is unsubstituted or substituted by halogen, hydroxyl, nitro, cyano, alkoxy, aryloxy or amino, cycloalkyl having 6 to 12 carbon atoms, benzyl or phenyl, which is unsubstituted or substituted by alkyl, alkoxy or alkylmercapto, each having 1 to 5 carbon atoms, hydroxy, nitro, cyano, amino, halogen, carboxamido, carbalkoxy, phenoxycarbonyl, benzyloxycarbonyl, —$SO_2NH_2$, N-substituted or N,N-disubstituted sulfonamide, acylamino or —$SO_2G$ or —COG, in which G is alkyl having 1 to 18 carbon atoms, which is unsubstituted or substituted by halogen, nitro, cyano, amino or alkoxy having 1 to 18 carbon atoms, or $M_4$, if Z is —CO—, is amino, mono- or di-alkylamino having, in each case, 1 to 5 carbon atoms in the alkyl moiety, alkoxy having 1 to 18 carbon atoms, phenoxy, carbalkoxy having 1 to 5 carbon atoms in the alkoxy moiety, or carboxamido which is N-substituted or N,N-disubstituted by alkyl having 1 to 3 carbon atoms and/or by phenyl, and $M_3$, if Z is —CO— or —$SO_2$—, has the meaning defined for $M_4$, or $M_3$, if Z is —CO—, is mono- or di-alkylamino, each having 1 to 5 carbon atoms in the alkyl moiety, alkoxy having 1 to 5 carbon atoms or phenoxy, Z is —CO— or —$SO_2$—, $R_{20}$ is hydrogen, alkyl having 1 to 12 carbon atoms, benzyl, phenyl, thienyl, cycloalkyl having 6 to 12 carbon atoms, alkoxy having 1 to 5 carbon atoms, alkylmercapto having 1 to 4 carbon atoms, halogen, benzoyl, benzoyloxyalkyl having 1 to 5 carbon atoms in the alkyl moiety, benzoylamino, mono- or di-alkylsulfonamide having, in each case, 1 to 5 carbon atoms in the alkyl moiety, or —$NHCOC_nH_{2n+1}$, in which n is 1 to 5, and $A_1$, $R_{11}$, $R_{12}$, $R_{13}$, $R_{17}$ and r are as defined in claim 7.

9. A recording material according to claim 8, wherein the yellow coupler has the formula

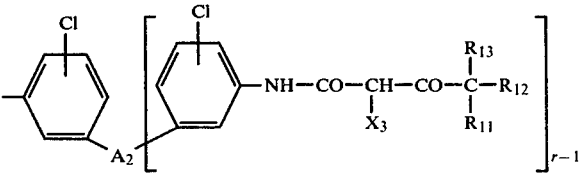

in which $A_2$ is a diazole, triazole, oxazole, thiazole, oxadiazole, thiadiazole, diazolone, triazolone, benzoxazole, benzthiazole or benzimidazole radical with at least one ballast group and, if desired, further substituents and $R_{11}$, $R_{12}$, $R_{13}$, $X_3$ and r are as defined in claim 8.

10. A recording material according to claim 9, wherein the yellow coupler has the formula

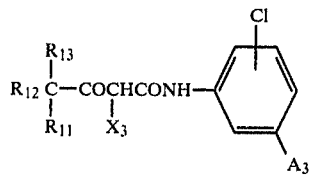

in which $A_3$ is a benzimidazole, benzoxazole, oxadiazole, thiadiazole, diazolone, triazolone or triazole radical with at least one ballast group and, if desired, further substituents and $R_{11}$, $R_{12}$, $R_{13}$ and $X_3$ are as defined in claim 9.

11. A recording material according to claim 9, wherein the yellow coupler has the formula

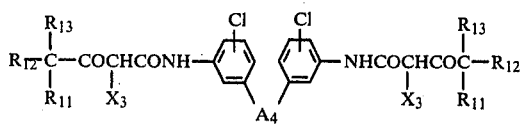

in which $A_4$ is a triazole radical with at least one ballast group and, if desired, further substituents and $R_{11}$, $R_{12}$, $R_{13}$ and $X_3$ are as defined in claim 9.

12. A recording material according to any one of claims 9 to 11, wherein the further substituents are alkyl, alkoxy, hydroxyalkyl, halogenoalkyl or alkylmercapto, each having 1 to 4 carbon atoms, halogen, amino, hydroxyl, carbalkoxy having 1 to 4 carbon atoms in the alkoxy moiety, —CN, —CONH$_2$ and/or —NHCOR$_{21}$, in which $R_{21}$ is alkyl having 1 to 4 carbon atoms or alkoxyalkyl having 2 to 4 carbon atoms, and the ballast group is alkyl, alkoxy, cycloalkoxy, alkoxyalkyl, alkoxycycloalkyl, cycloalkoxyalkyl, aralkyl, phenoxyalkyl, which can be substituted by halogen or alkyl having 1 to 10 carbon atoms, alkyl- or dialkylaminoalkyl, substituted or unsubstituted aryl- or diarylaminoalkyl, alkylmercaptoalkyl or substituted or unsubstituted arylmercaptoalkyl, in which the sum of the carbon atoms is 5 to 40 in each case; or also —COOR$_{22}$, COR$_{22}$, —NR$_{22}$R$_{23}$, —CONR$_{22}$R$_{23}$, —NR$_{23}$COR$_{22}$, —NR$_{23}$COR$_{24}$, —SO$_2$R$_{22}$, —SO$_2$NR$_{22}$R$_{23}$ or —NR$_{25}$SO$_2$R$_{22}$, in which $R_{22}$ is alkyl having 5 to 40 carbon atoms or cycloalkyl having 5 to 12 carbon atoms, $R_{23}$ is hydrogen or alkyl having 1 to 12 carbon atoms and $R_{24}$ is alkoxyalkyl having 5 to 20 carbon atoms or phenoxyalkyl which has 1 to 12 carbon atoms in the alkyl moiety and can be substituted on the phenyl ring by alkyl having 1 to 10 carbon atoms.

13. A recording material according to claim 10, wherein the yellow coupler has the formula

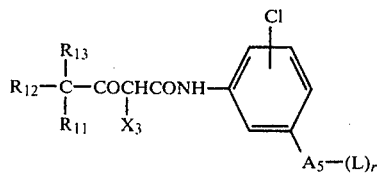

in which $A_5$ is a benzimidazole, benzoxazole, oxadiazole, thiadiazole, diazolone, triazolone or triazole radical, which can be substituted by alkyl, alkoxy and/or halogenoalkyl, each having 1 to 4 carbon atoms, or alkoxyalkyl having 2 to 4 carbon atoms, L is alkyl, alkoxy, alkoxyalkyl, phenylalkyl or phenoxyalkyl having 5 to 30 carbon atoms, —NHCOR$_{22}$ or —NR$_{23}$COR$_{24}$, in which $R_{22}$ is alkyl having 5 to 40 carbon atoms or cycloalkyl having 5 to 12 carbon atoms, $R_{23}$ is hydrogen or alkyl having 1 to 12 carbon atoms and $R_{24}$ is alkoxyalkyl having 5 to 20 carbon atoms or phenoxyalkyl which has 1 to 12 carbon atoms in the alkyl moiety and can be substituted on the phenyl ring by alkyl having 1 to 10 carbon atoms, and r is 1 or 2 and $A_3$, $R_{11}$, $R_{12}$, $R_{13}$ and $X_3$ are as defined in claim 10.

14. A recording material according to claim 13, wherein the yellow coupler has the formula

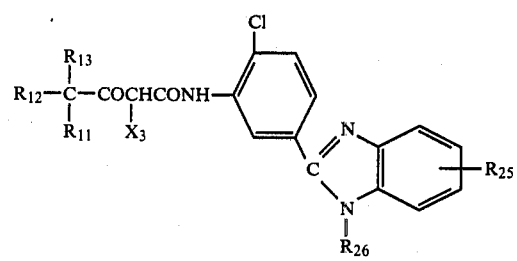

in which $R_{25}$ is hydrogen or alkyl, alkoxy and/or halogenoalkyl, each having 1 to 4 carbon atoms, and $R_{26}$ is alkyl, alkoxyalkyl, phenylalkyl or phenoxyalkyl having 8 to 30 carbon atoms and $R_{11}$, $R_{12}$, $R_{13}$ and $X_3$ are as defined in claim 13.

15. A recording material according to claim 13, wherein the yellow coupler has the formula

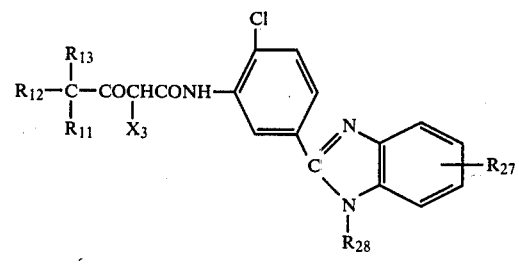

in which $R_{27}$ is alkyl, alkoxy, alkoxyalkyl, phenylalkyl or phenoxyalkyl having 8 to 30 carbon atoms, —NR$_{23}$COR$_{22}$ or —NR$_{23}$COR$_{24}$, $R_{22}$ is alkyl having 5 to 40 carbon atoms or cycloalkyl having 5 to 12 carbon atoms, $R_{23}$ is hydrogen or alkyl having 1 to 12 carbon atoms, $R_{24}$ is alkoxyalkyl having 5 to 20 carbon atoms or phenoxyalkyl which has 1 to 12 carbon atoms in the alkyl moiety and can be substituted on the phenyl ring by alkyl having 1 to 10 carbon atoms, and $R_{28}$ is hydrogen or alkyl or halogenoalkyl, each having 1 to 4 carbon atoms, and $R_{11}$, $R_{12}$, $R_{13}$ and $X_3$ are as defined in claim 13.

16. A recording material according to claim 13, wherein the yellow coupler has the formula

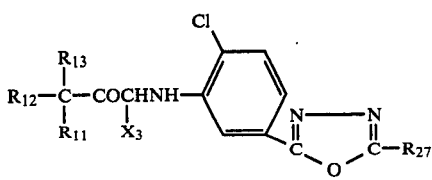

in which $R_{27}$ is alkyl, alkoxyalkyl, phenylalkyl or phenoxyalkyl having 8 to 30 carbon atoms, $-NR_{23}COR_{22}$ or $-NR_{23}COR_{24}$, $R_{22}$ is alkyl having 5 to 40 carbon atoms or cycloalkyl having 5 to 12 carbon atoms, $R_{23}$ is hydrogen or alkyl having 1 to 12 carbon atoms, $R_{24}$ is alkoxyalkyl having 5 to 20 carbon atoms or phenoxyalkyl which has 1 to 12 carbon atoms in the alkyl moiety and in which the phenyl ring can be substituted by alkyl having 1 to 10 carbon atoms and $R_{11}$, $R_{12}$, $R_{13}$ and $X_3$ are as defined in claim 13.

17. A recording material according to claim 14, wherein $R_{11}$, $R_{12}$ and $R_{13}$ are methyl.

18. A recording material according to claim 15 wherein $R_{11}$, $R_{12}$ and $R_{13}$ are methyl.

19. A recording material according to claim 16, wherein $R_{11}$, $R_{12}$ and $R_{13}$ are methyl.

20. A recording material according to claim 14, wherein $R_{25}$ and $R_{26}$ are alkyl having 8 to 30 carbon atoms.

21. A recording material according to claim 11, wherein the yellow coupler has the formula in which n is 8 to 25 and $X_3$ is as defined in claim 11.

22. A recording material according to claim 13, wherein the yellow coupler has the formula

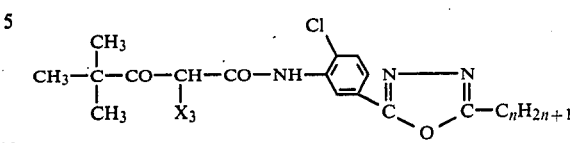

in which n is 8 to 25 and $X_3$ is as defined in claim 13.

23. A recording material according to claim 14, wherein the yellow coupler has the formula

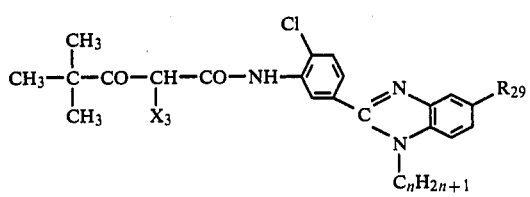

in which n is 8 to 25 and $R_{29}$ is hydrogen, methoxy or trifluoromethyl and $X_3$ is as defined in claim 14.

24. A process, for colour photography, for the production of a yellow image by colour development of a recording material according to claim 1, which has been exposed image-wise.

25. The yellow images produced by the process according to claim 24.

* * * * *

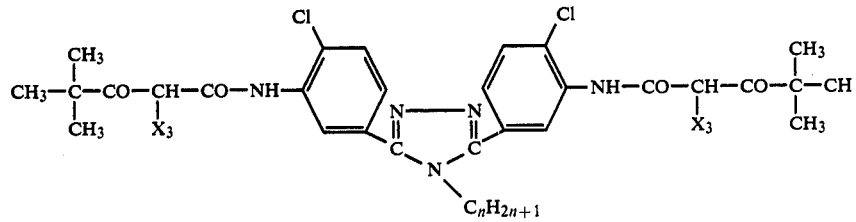

UNITED STATES PATENT AND TRADEMARK OFFICE
CERTIFICATE OF CORRECTION

PATENT NO. : 4,268,591
DATED : May 19, 1981
INVENTOR(S) : Paul Tschopp

It is certified that error appears in the above—identified patent and that said Letters Patent is hereby corrected as shown below:

Column 5, line 19, delete "$\searrow_s\swarrow$"

and insert -- $\searrow_Y\swarrow$ --.

Signed and Sealed this

Sixth Day of October 1981

[SEAL]

Attest:

GERALD J. MOSSINGHOFF

Attesting Officer   Commissioner of Patents and Trademarks